United States Patent
Jung et al.

(10) Patent No.: US 11,669,961 B2
(45) Date of Patent: Jun. 6, 2023

(54) IMAGE PROCESSING DEVICE AND CALCIFICATION ANALYSIS SYSTEM INCLUDING THE SAME

(71) Applicant: ELECTRONICS AND TELECOMMUNICATIONS RESEARCH INSTITUTE, Daejeon (KR)

(72) Inventors: Ho-Youl Jung, Daejeon (KR); Jae Hun Choi, Daejeon (KR)

(73) Assignee: ELECTRONICS AND TELECOMMUNICATIONS RESEARCH INSTITUTE, Daejeon (KR)

(*) Notice: Subject to any disclaimer, the term of this patent is extended or adjusted under 35 U.S.C. 154(b) by 211 days.

(21) Appl. No.: 16/950,573

(22) Filed: Nov. 17, 2020

(65) Prior Publication Data
US 2021/0174498 A1   Jun. 10, 2021

(30) Foreign Application Priority Data
Dec. 10, 2019   (KR) .................. 10-2019-0163934

(51) Int. Cl.
*G06T 7/00*   (2017.01)
*A61B 6/03*   (2006.01)
(Continued)

(52) U.S. Cl.
CPC ............ *G06T 7/0012* (2013.01); *A61B 6/032* (2013.01); *A61B 6/466* (2013.01); *A61B 6/503* (2013.01);
(Continued)

(58) Field of Classification Search
CPC .............. G06T 7/0012; G06T 2200/04; G06T 2207/10081; G06T 2207/20081;
(Continued)

(56) References Cited

U.S. PATENT DOCUMENTS 8,150,151 B2   4/2012   Gori et al.
2008/0194943 A1*  8/2008   Lorenz .................. G06T 7/0012
                                                                  600/419
(Continued)

FOREIGN PATENT DOCUMENTS

KR   1020120130164 A   11/2012

OTHER PUBLICATIONS

Kim et al. "Automatic CAC voxel classification with multi-scale CNN architecture." 2019 International Conference on Information and Communication Technology Convergence (ICTC). IEEE, Oct. 2019. (Year: 2019).*

(Continued)

*Primary Examiner* — Katrina R Fujita

(57) ABSTRACT

The image processing device includes a voxel extractor, a learner, and a predictor. The voxel extractor extracts a target voxel and neighboring voxels adjacent to the target voxel from a 3D image. The learner generates vectors corresponding to the target voxel and the neighboring voxels, respectively, generates vector weights corresponding to each of the vectors, based on the vectors and a parameter group, and adjusts the parameter group, based on an analysis result of the target voxel generated by applying the vector weights to the vectors. The predictor generates vectors corresponding to the target voxel and the neighboring voxels, respectively, generates correlation weights among the vectors by applying a parameter group to the vectors, generates vector weights corresponding to each of the vectors by applying the correlation weights to the vectors, and generates an analysis result of the target voxel by applying the vector weights to the vectors.

16 Claims, 7 Drawing Sheets

(51) Int. Cl.
*A61B 6/00* (2006.01)
*G06N 3/04* (2023.01)
*G06N 3/08* (2023.01)
*G06V 10/82* (2022.01)

(52) U.S. Cl.
CPC ............... *A61B 6/504* (2013.01); *G06N 3/04* (2013.01); *G06N 3/08* (2013.01); *G06V 10/82* (2022.01); *G06T 2200/04* (2013.01); *G06T 2207/10081* (2013.01); *G06T 2207/20081* (2013.01); *G06T 2207/20084* (2013.01); *G06T 2207/30048* (2013.01); *G06T 2207/30101* (2013.01)

(58) Field of Classification Search
CPC .......... G06T 2207/20084; G06V 10/82; A61B 6/032; A61B 6/466; A61B 6/503; A61B 6/504
See application file for complete search history.

(56) References Cited

U.S. PATENT DOCUMENTS

| | | | | |
|---|---|---|---|---|
| 2009/0080740 | A1* | 3/2009 | Shinagawa | G06T 7/0012 382/131 |
| 2011/0118595 | A1* | 5/2011 | Aulbach | A61B 6/504 600/425 |
| 2012/0283530 | A1 | 11/2012 | Maynard et al. | |
| 2014/0003695 | A1* | 1/2014 | Dean | A61F 2/30942 382/131 |
| 2017/0003366 | A1* | 1/2017 | Jafari-Lhouzani | G06T 7/0012 |
| 2017/0011534 | A1* | 1/2017 | Costa | G06T 7/62 |
| 2017/0091935 | A1* | 3/2017 | Leon | A61B 6/032 |
| 2018/0211381 | A1 | 7/2018 | Chae et al. | |
| 2018/0240235 | A1 | 8/2018 | Mazo | |
| 2019/0090834 | A1* | 3/2019 | Pauly | A61B 6/025 |
| 2019/0164037 | A1 | 5/2019 | Kim et al. | |

OTHER PUBLICATIONS

Wang et al. "Central focused convolutional neural networks: Developing a data-driven model for lung nodule segmentation." Medical image analysis 40 (2017): 172-183. (Year: 2017).*

Lessmann et al., "Automatic Calcium Scoring in Low-Dose Chest CT Using Deep Neural Networks With Dilated Convolutions," Feb. 2018, IEEE, vol. 37, No. 2, pp. 615-625.

Wolterink et al., "An automatic machine learning system for coronary calcium scoring in clinical non-contrast enhanced, ECG-triggered cardiac CT," 2014, Proc. of SPIE, vol. 9035, pp. 90350E-1-90350E-8.

* cited by examiner

IMAGE PROCESSING DEVICE AND CALCIFICATION ANALYSIS SYSTEM INCLUDING THE SAME

CROSS-REFERENCE TO RELATED APPLICATIONS

This application claims priority under 35 U.S.C. § 119 to Korean Patent Application No. 10-2019-0163934 filed on Dec. 10, 2019, in the Korean Intellectual Property Office, the disclosures of which are incorporated by reference herein in their entireties.

BACKGROUND

Embodiments of the inventive concept described herein relate to image processing, and more particularly, relate to an image processing device and a calcification analysis system including the same.

Cardiovascular disease is one of the diseases with a high mortality rate in modern society. The mechanism of onset of cardiovascular disease is not accurately known, but environmental factors such as lifestyle are known as risk factors for cardiovascular disease. Coronary artery calcification is a phenomenon in which calcium in the blood is deposited in the coronary arteries of the heart. The coronary arteries may supply oxygen and nutrients to the heart muscle by supplying the blood to the heart. As coronary artery calcification progresses, blood vessels become narrower, and the likelihood of cardiovascular disease may increase.

Traditionally, for coronary artery calcification, doctors analyzed cardiac CT (Computed Tomography) images and passively searched for the calcification area. In recent years, with the development of image processing technology, an image processing device searches for candidate groups in the calcification area, and doctors correct errors in the candidate groups, and semi-automatically search for the calcification area. However, when there are many such errors, there are many tasks to be corrected by the doctor. Accordingly, there is a need for a method of improving an accuracy of the search for the calcification region, and ultimately fully automatically searching the calcification region.

SUMMARY

Embodiments of the inventive concept provide an image processing device and a calcification analysis system including the same, which improves an accuracy of analysis of a 3D image and improves an accuracy of analysis of coronary artery calcification.

According to an embodiment of the inventive concept, an image processing device includes a voxel extractor and a learner. The voxel extractor extracts a target voxel and neighboring voxels adjacent to the target voxel from a 3D image. The learner generates vectors corresponding to the target voxel and the neighboring voxels, respectively, generates vector weights corresponding to each of the vectors, based on the vectors and a parameter group, and adjusts the parameter group, based on an analysis result of the target voxel generated by applying the vector weights to the vectors.

According to an embodiment, the number of the neighboring voxels may be $(2n+1)^3-1$ with respect to a natural number 'n'.

According to an embodiment, the learner may generate correlation weights among the vectors by applying the parameter group to the vectors, and may generate the vector weights by applying the correlation weights to the vectors. According to an embodiment, the learner may generate a vector weight corresponding to a target vector by applying correlation weights between the target vector and the vectors among the correlation weights to the vectors.

According to an embodiment, the learner may generate the vectors through a convolutional neural network operation on each of the target voxel and the neighboring voxels. According to an embodiment, the learner may generate the vectors by merging a result of a convolutional neural network operation on each of the target voxel and the neighboring voxels and a result of a dilated convolutional neural network operation on each of the target voxel and the neighboring voxels.

According to an embodiment, the learner may adjust the parameter group until the analysis result is within a reference error from a preset result.

According to an embodiment, the 3D image may be a computed tomography image, and the analysis result may be a calcification index.

According to an embodiment of the inventive concept, an image processing device includes a voxel extractor and a predictor. The voxel extractor extracts a target voxel and neighboring voxels adjacent to the target voxel from a 3D image. The predictor generates vectors corresponding to the target voxel and the neighboring voxels, respectively, generates correlation weights among the vectors by applying a parameter group to the vectors, generates vector weights corresponding to each of the vectors by applying the correlation weights to the vectors, and generates an analysis result of the target voxel by applying the vector weights to the vectors.

According to an embodiment, the number of the neighboring voxels may be $(2n+1)^3-1$ with respect to a natural number 'n'.

According to an embodiment, the predictor may generate target correlation weights among a target vector and the vectors, based on the target vector corresponding to the target voxel among the vectors, the vectors, and the parameter group. According to an embodiment, the predictor may generate a vector weight corresponding to the target vector by adding values obtained by multiplying each of the vectors to each of the target correlation weights. According to an embodiment, the parameter group may include parameter values depending on a correlation of the vectors for each of the vectors.

According to an embodiment, the voxel extractor may set each of a plurality of voxels included in the 3D image as the target voxel, and extracts the neighboring voxels, based on the set target voxel. According to an embodiment, the predictor may calculate a calcification index of the 3D image, based on analysis results of each of the voxels.

According to an embodiment of the inventive concept, a calcification analysis system includes a computed tomography device and an image processing device. The computed tomography device generates a 3D computed tomography image. The image processing device extracts a target voxel and neighboring voxels adjacent to the target voxel from the 3D computed tomography image, generates vectors corresponding to the target voxel and the neighboring voxels, respectively, generates vector weights corresponding to each of the vectors, based on a correlation among the vectors, and calculates a calcification index of the target voxel by applying the vector weights to the vectors.

According to an embodiment, the image processing device may include a learner that generates correlation weights among the vectors by applying a parameter group to the vectors, generates the vector weights by applying the correlation weights to the vectors, and adjusts the parameter group, based on the calcification index. According to an embodiment, the learner may adjust the parameter group until the calcification index is within a reference error from a preset result, and the adjusted parameter group may be stored in a learning model database.

According to an embodiment, the image processing device may include a predictor that generates correlation weights among the vectors by applying a parameter group provided from a learning model database to the vectors, generates the vector weights by applying the correlation weights to the vectors, and calculates the calcification index of the target voxel by applying the vector weights to the vectors. According to an embodiment, the image processing device may further include a voxel extractor that sets each of a plurality of voxels included in the 3D image as the target voxel and extracts the neighboring voxels, based on the set target voxel, and the predictor may calculate a calcification index of the 3D image, based on analysis results of each of the voxels.

BRIEF DESCRIPTION OF THE FIGURES

The above and other objects and features of the inventive concept will become apparent by describing in detail exemplary embodiments thereof with reference to the accompanying drawings.

DETAILED DESCRIPTION

Hereinafter, embodiments of the inventive concept will be described clearly and in detail such that those skilled in the art may easily carry out the inventive concept.

Figure 1:
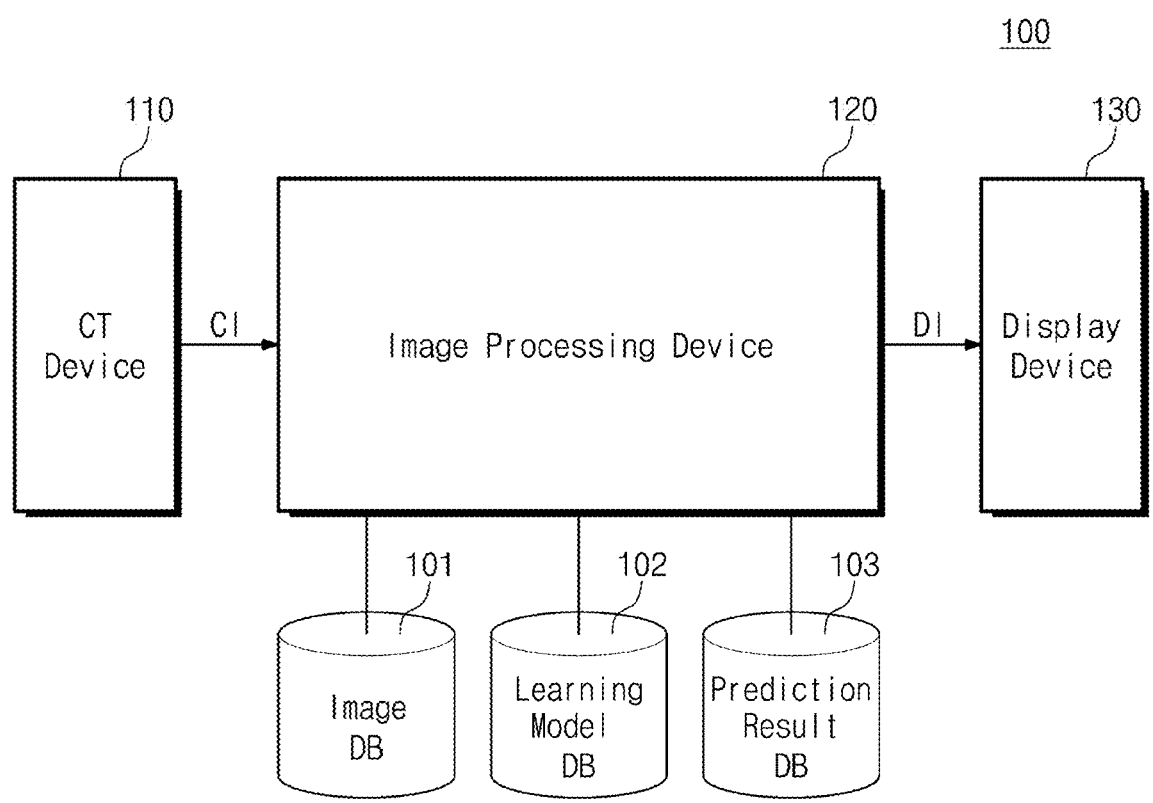
FIG. 1 is a diagram illustrating a calcification analysis system according to an embodiment of the inventive concept.

FIG. 1 is a diagram illustrating a calcification analysis system according to an embodiment of the inventive concept. Referring to FIG. 1, a calcification analysis system 100 includes a computed tomography (CT) device 110, an image processing device 120, and a display device 130. Unlike illustrated, the image processing device 120 and the display device 130 may be included in the computed tomography device 110.

The calcification analysis system 100 may be used to determine a calcification of a user's coronary artery and calculate a calcification index. However, the inventive concept is not limited thereto, and the calcification analysis system 100 may be used to determine the calcification of other organs of a user, and to calculate the calcification index. Further, the calcification analysis system 100 may be used to determine a lesion of a user that can be read by a computed tomography image.

The computed tomography device 110 may generate a 3D image CI, that is, a 3D computed tomography image. As an example, the computed tomography device 110 may irradiate light such as X-ray to a subject such as a user. The light is projected to the user, and the computed tomography device 110 may receive the projected light. A light source may output the light while rotating around the subject. The computed tomography device 110 may generate the 3D image CI by receiving the light irradiated from various directions. The 3D image CI may be output to the image processing device 120 and an image database 101 may be implemented by performing databaseization of the 3D image CI. The databaseization of the image database 101 may be performed on a server or storage medium of the image processing device 120, or a separate server or separate storage medium.

The image processing device 120 may analyze the 3D image CI to determine the user's calcification and calculate the calcification index. The image processing device 120 may learn a learning model using the 3D image CI. The learning model may be a modeled structure to determine the calcification and calculate the calcification index through the 3D image CI. A learning model database 102 may be implemented by performing databaseization of the learning model. The databaseization of the learning model database 102 may be performed on a server or storage medium of the image processing device 120, or a separate server or storage medium. The learning model may be used to determine the user's calcification.

The 3D image CI may be analyzed in units of voxels. The image processing device 120 may extract a target voxel and neighboring voxels adjacent to the target voxel to determine the calcification associated with the target voxel. The target voxel is an object to be analyzed in the 3D image CI, and all voxels of the 3D image CI may be sequentially set as the target voxel. The neighboring voxels may mean voxels arranged adjacent to the target voxel in a 3D space. For example, 26 voxels surrounding the target voxel of a hexahedron may be extracted as the neighboring voxels. The number of the neighboring voxels may be $(2n+1)^3-1$, and 'n' is a natural number and may be the number of voxels adjacent in a specific direction.

The image processing device 120 may generate vectors corresponding to each of the target voxel and the neighboring voxels through a neural network operation on each of the target voxel and the neighboring voxels. As an example, the neural network operation may be performed by a convolutional neural network (CNN) layer. For example, the neural network operation may be performed in parallel by the convolutional neural network (CNN) layer and a dilated CNN layer, and the results may be merged.

The image processing device 120 may generate correlation weights among the vectors by applying parameter values representing a correlation between vectors to vectors. The learning model may be managed as the parameter values in the learning model database 102. The image processing device 120 may generate vector weights corresponding to the vectors by applying the correlation weights to the vectors. The image processing device 120 may calculate the calcification index of the target voxel by applying the vector weights to the vectors. These operations are performed using a neighbor attention model, and the correlation weights and the vector weights may be generated using the neighbor attention model.

In a learning step, the image processing device 120 may adjust a parameter group including the parameter values, based on an analysis result of the target voxel (i.e., the calcification index). For example, the image processing device 120 may adjust the parameter group until the analysis result of the target voxel is within a reference error from a result of a known target voxel. The adjusted parameter group may be updated in the learning model database 102.

In a prediction step, the image processing device 120 may determine the user's calcification, based on the analysis result of the target voxel (i.e., the calcification index). For example, the image processing device 120 may calculate a user's final calcification index by merging the calcification indexes of each voxel of the 3D image CI. A prediction result database 103 may be implemented by performing databaseization of such analysis results. The databaseization of the prediction result database 103 may be performed on a server or storage medium of the image processing device 120, or a separate server or separate storage medium.

The display device 130 may receive a display image DI corresponding to the 3D image CI from the image processing device 120. The image processing device 120 may generate the display image DI by converting the 3D image CI into a displayable image. The display device 130 may display not only the CT image, but also an image related to the user's calcification analysis result.

Figure 2:
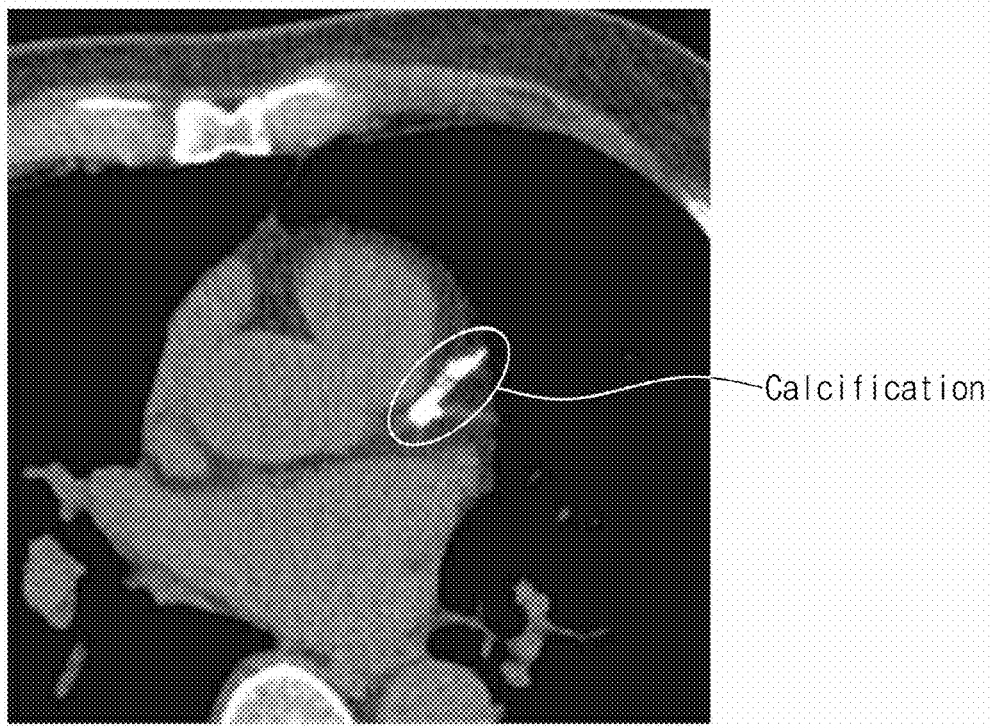
FIG. 2 is a diagram describing a calcification of a coronary artery described in FIG. 1.

FIG. 2 is a diagram describing a calcification of a coronary artery described in FIG. 1. It will be understood that FIG. 2 illustrates a part of the 3D image CI of a heart region obtained by the computed tomography device 110 of FIG. 1. The coronary artery calcification is a phenomenon in which calcium in the blood is deposited in the coronary arteries of the heart. The image processing device 120 of FIG. 1 may calculate the calcification index of the coronary arteries by analyzing a Hounsfield Unit (HU) of each voxel, based on the above-described learning model. In general, voxels of 130 HU or more may be voxels exhibiting the calcification. However, as illustrated in FIG. 2, a bone image also may be 130 HU or more voxels. The calcification analysis system 100 of FIG. 1 may calculate the calcification index of the coronary artery in consideration of anatomical information of a blood vessel without a separate search process by applying the target voxel and the neighboring voxels to a learned neighbor attention model. Accordingly, the accuracy of determining calcification and the accuracy of the calcification index may be improved.

Figure 3:
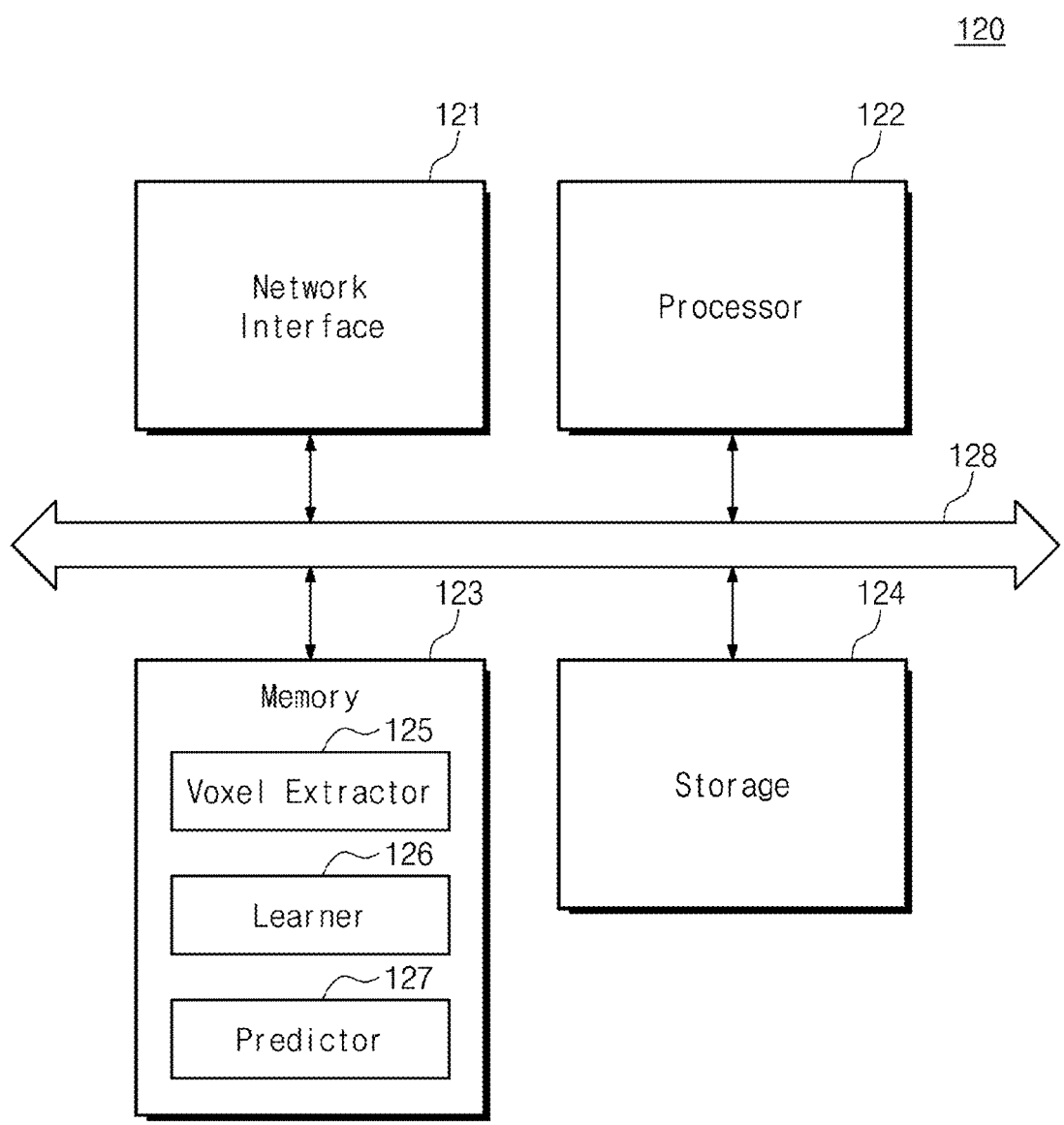
FIG. 3 is an exemplary block diagram of an image processing device of FIG. 1.

FIG. 3 is an exemplary block diagram of an image processing device of FIG. 1. Referring to FIG. 3, the image processing device 120 may include a network interface 121, a processor 122, a memory 123, storage 124, and a bus 128.

The network interface 121 is configured to communicate with the computed tomography device 110 of FIG. 1, the display device 130 of FIG. 1, or an external electronic device. The network interface 121 may provide data received to the image processing device 120, such as the 3D image CI, to the processor 122, the memory 123, or the storage 124 through the bus 128.

The processor 122 may function as a central processing unit of the image processing device 120. The processor 122 may perform control operations and calculation operations required for data management, learning, and prediction of the image processing device 120. For example, under the control of the processor 122, the network interface 121 may receive the 3D image CI from the computed tomography device 110. Under the control of the processor 122, the parameter group of the learning model may be adjusted, and the analysis result such as the calcification index may be calculated using the learning model. The processor 122 may operate by utilizing a computational space of the memory 123, and may read files for driving an operating system and executable files of an application from the storage 124. The processor 122 may execute the operating system and various applications.

The memory 123 may store data and process codes processed or scheduled to be processed by the processor 122. For example, the memory 123 may store the 3D image CI for processing, information for managing the 3D image CI, information for generating the parameter group of the learning model, information for calculating the analysis result such as the calcification index, and information for constructing the learning model. The memory 123 may be used as a main memory device of the image processing device 120. The memory 123 may include a DRAM (a Dynamic RAM), an SRAM (a Static RAM), a PRAM (a Phase-change RAM), an MRAM (a Magnetic RAM), a FeRAM (a Ferroelectric RAM), an RRAM (a Resistive RAM), etc.

A voxel extractor 125, a learner 126, and a predictor 127 may be loaded into the memory 123 and may be executed. The voxel extractor 125, the learner 126, and the predictor 127 may be a part of the computational space of the memory 123. In this case, the voxel extractor 125, the learner 126, and the predictor 127 may be implemented in firmware or software. For example, the firmware may be stored in the storage 124 and may be loaded into the memory 123 when the firmware is executed. The processor 122 may execute the firmware loaded in the memory 123. However, the inventive concept is not limited thereto, and the voxel extractor 125, the learner 126, and the predictor 127 may be implemented with hardware such as a dedicated logic circuit such as a Field Programmable Gate Array (FPGA) or an Application Specific Integrated Circuit (ASIC).

The voxel extractor 125 may extract the target voxel and the neighboring voxels adjacent to the target voxel from the 3D image CI. The extracted target voxel and the neighboring voxels are grouped into an input voxel group, and may be used to calculate an analysis result of the target voxel. The voxel extractor 125 may sequentially set each voxel of the 3D image CI as the target voxel. The neighboring voxels may be voxels disposed adjacent to the target voxel in the 3D space. To calculate the analysis result of the target voxel, by extracting not only the target voxel but also the neighboring voxels, it is possible to consider which organ of the human body a region corresponding to the target voxel is. Therefore, the accuracy of analysis results such as the calcification of coronary arteries may be improved.

The learner 126 may adjust the parameter group by training the learning model using the input voxel group. The learner 126 may generate the vectors corresponding to the target voxel and the neighboring voxels, respectively, through a CNN operation on the input voxel group. The learner 126 may generate the correlation weights among the vectors by applying the parameter group to the vectors. The learner 126 may generate the vector weights corresponding to the vectors by applying the correlation weights to the vectors. The learner 126 may generate an analysis result related to the calcification index of the target voxel by applying the vector weights to the vectors. The learner 126 may adjust the parameter group until the analysis result is within a reference error from a preset result.

The predictor 127 may calculate the calcification index of the 3D image CI and may determine the calcification of the coronary artery by using the learning model. The predictor 127 may generate the vectors corresponding to the target voxel and the neighboring voxels, respectively, through the CNN operation on the input voxel group of the 3D image CI. Like the learner 126, the predictor 127 may generate the correlation weights and the vector weights, based on the vectors and the parameter group, and may generate the analysis result related to the calcification index of the target voxel. The predictor 127 may calculate the final calcification index by considering the calcification index of each of the voxels of the 3D image CI, and may determine the calcification of the coronary artery.

The storage 124 may store data generated for long-term storage by an operating system or applications, a file for driving an operating system, or an executable file of applications. For example, the storage 124 may store files for execution of the voxel extractor 125, the learner 126, and the predictor 127. The storage 124 may be used as an auxiliary memory device of the image processing device 120. The storage 124 may include a flash memory, a phase-change RAM (a PRAM), a magnetic RAM (an MRAM), a ferroelectric RAM (a FeRAM), a resistive RAM (an RRAM), etc.

The bus 128 may provide a communication path among components of the image processing device 120. The network interface 121, the processor 122, the memory 123, and the storage 124 may exchange data with one another through the bus 128. The bus 128 may be configured to support various types of communication formats used in the image processing device 120.

Figure 4:
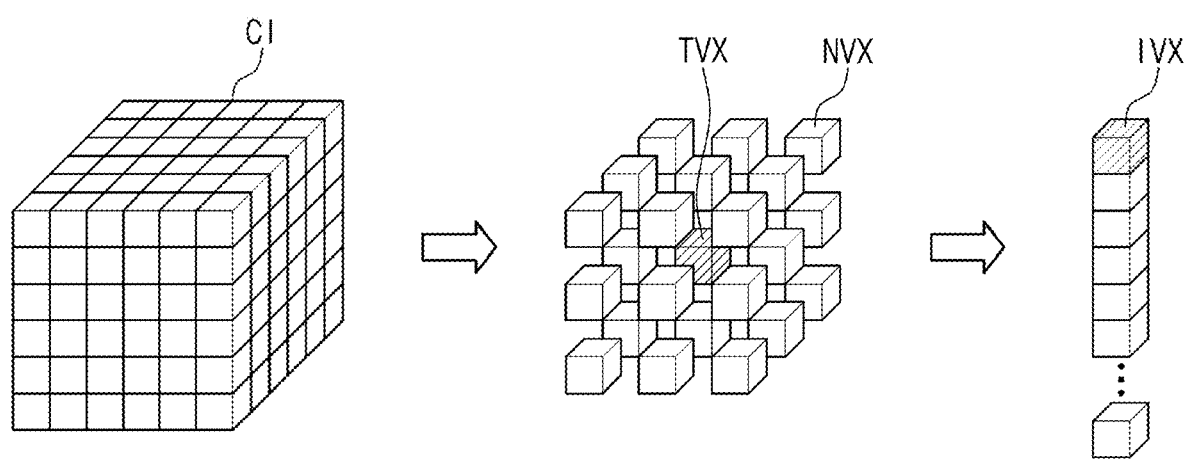
FIG. 4 is a diagram describing a voxel extraction for learning or prediction in an image processing device of FIGS. 1 and 3.

FIG. 4 is a diagram describing a voxel extraction for learning or prediction in an image processing device of FIGS. 1 and 3. Referring to FIG. 4, the 3D image CI includes a plurality of voxels. The image processing device 120 or the voxel extractor 125 of FIG. 3 may set a target voxel TVX from the voxels and may extract neighboring voxels NVX of the target voxel TVX. The voxel extractor 125 may sequentially set each of the plurality of voxels as the target voxel TVX. As the set target voxel TVX is changed, the neighboring voxels NVX may also be changed.

Based on the target voxel TVX represented as a hexahedron, neighboring voxels surrounding the target voxel TVX in the 3D space may be extracted as the neighboring voxels NVX. For example, as illustrated in FIG. 4, 26 voxels surrounding the target voxel TVX may be extracted as the neighboring voxels NVX. However, the number of the neighboring voxels NVX is not limited to FIG. 4. In FIG. 4, voxels having one voxel distance, based on the target voxel TVX, are illustrated as the neighboring voxels NVX, but voxels having two or less voxel distances may be extracted as the neighboring voxels NVX. In this case, the number of neighboring voxels may be 124, which is $(2n+1)^3-1$ (n=2).

The extracted target voxel TVX and the extracted neighboring voxels NVX may be grouped into an input voxel group IVX such that they may be input to the learning model. The input voxel group IVX may be used to determine the calcification index of the target voxel TVX using the learning model. By applying the voxels adjacent to the target voxel to the learning model, the calcification index of the coronary artery may be calculated in consideration of anatomical information of the blood vessel. Accordingly, the accuracy of determining calcification and the accuracy of the calcification index may be improved.

Figure 5:
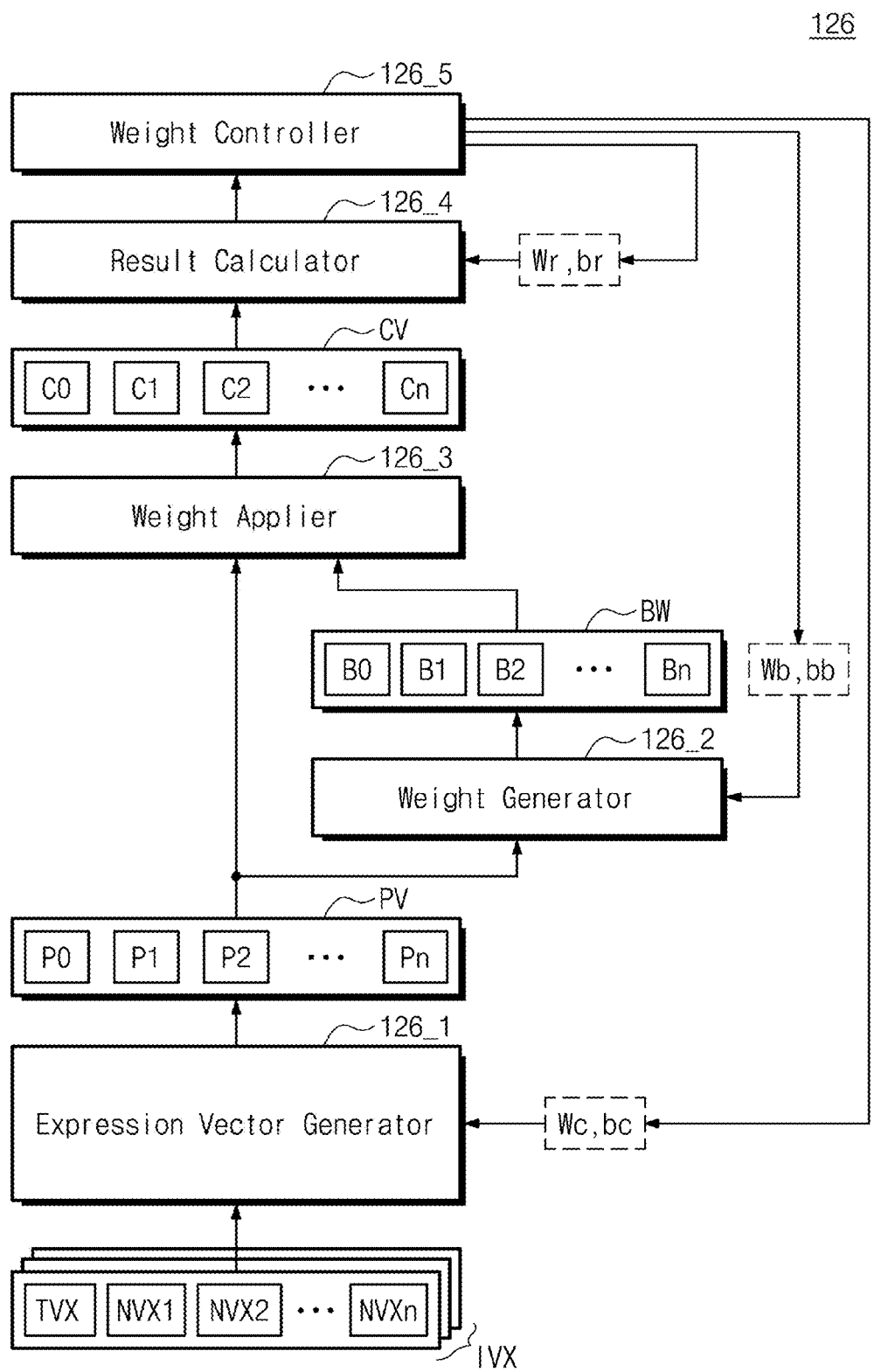
FIG. 5 is an exemplary block diagram of a learner of FIG. 3.

FIG. 5 is an exemplary block diagram of a learner of FIG. 3. The learner 126 of FIG. 5 will be understood as an exemplary configuration that trains the learning model, based on the input voxel group IVX described in FIG. 4 and determines the parameter group. Referring to FIG. 5, the learner 126 may include an expression vector generator 126_1, a weight generator 126_2, a weight applier 126_3, a result calculator 126_4, and a weight controller 126_5. As described above, each of the components included in the learner 126 may be implemented with hardware, firmware, software, or a combination thereof.

The expression vector generator 126_1 may generate an expression vector PV through the neural network operation on the input voxel group IVX. The expression vector PV may include a plurality of vectors P0, P1, P2, ..., and Pn respectively corresponding to the target voxel TVX and the neighboring voxels NVX1, NVX2, ..., and NVXn. Each of the vectors P0 to Pn will be understood as an abstracted element indicating whether the corresponding voxel is calcified. The expression vector generator 126_1 may generate the expression vector PV through the convolutional neural network (CNN) model used for image analysis. The expression vector generator 126_1 may generate the vectors P0 to Pn corresponding to each of the target voxel TVX and the neighboring voxels NVX1 to NVXn, based on a weight Wc and a bias bc of the CNN model. The weight Wc and the bias bc may be included in the above-described parameter group.

The expression vector generator 126_1 may use the CNN and the dilated CNN in parallel to analyze the input voxel group IVX. The dilated CNN may be a CNN that dilates a filtering region by adding zero padding to a filter (weight). The dilated CNN may analyze global features of each voxel by dilating the filtering region. That is, the expression vector generator 126_1 may increase a utility of each of the vectors P0 to Pn by analyzing overall features of each voxel through the dilated CNN, analyzing more local features through the CNN, and merging these analysis results.

The weight generator 126_2 may generate a vector weight group BW, based on the expression vector PV. The vector weight group BW may include vector weights B0, B1, B2, ..., and Bn respectively corresponding to the vectors P0 to Pn. Each of the vector weights B0 to Bn may be an indicator indicating an importance of the vector to be analyzed, to determine the calcification of the target voxel TVX. The weight generator 126_2 may generate the vector weights B0 to Bn so that the analysis result pays attention to a specific vector, using a neighbor attention mechanism. The weight generator 126_2 may generate a vector weight group BW, based on a weight Wb and a bias bb of the neighbor attention model. The weight Wb and the bias bb may be included in the above-described parameter group.

The weight generator 126_2 may generate the correlation weights for generating the vector weight group BW. The correlation weights may be an indicator indicating a correlation between vectors, a connection relationship between vectors, or importance between vectors. The correlation weights may be generated by applying the weight Wb and the bias bb of the neighbor attention model to the vectors P0 to Pn. For example, correlation weights Bij may be generated by Equation 1.

$$B_{ij} = \frac{\exp(e_{ij}^2)}{\sum_{j=0}^{n} \exp(e_{ij}^2)}, \text{ for } i, j = 0, \ldots, n \quad \text{[Equation 1]}$$

$$e_{ij}^2 = P_i W b P_j + bb, \text{ for } i, j = 0, \ldots, n$$

Referring to Equation 1, the weight generator 126_2 may generate the correlation weights Bij between vectors by applying the weight Wb and the bias bb to arbitrary two vectors and applying a softmax function to the application result.

The weight generator 126_2 may generate the vector weights B0 to Bn corresponding to the vectors P0 to Pn by applying the correlation weights Bij to the vectors P0 to Pn. For example, vector weights B0 to Bn and Bi may be generated based on Equation 2.

$$B_i = \sum_{j=0}^{n} B_{ij} P_j \qquad \text{[Equation 2]}$$

Referring to Equation 2, the weight generator 126_2 may generate the vector weights B0 to Bn and Bi respectively corresponding to the vectors P0 to Pn by multiplying the correlation weights Bij by each of the vectors P0 to Pn and adding the results.

The weight applier 126_3 may apply the vector weights B0 to Bn to the vectors P0 to Pn. The weight applier 126_3 may generate an application result group CV by multiplying a vector by the vector weight corresponding to each of the vectors P0 to Pn. The application result group CV may include intermediate results C0, C1, C2, . . . , and Cn corresponding to each of the target voxel TVX and the neighboring voxels NVX. Each of the intermediate results C0 to Cn may be a result obtained by multiplying each of the vectors P0 to Pn by each of the vector weights B0 to Bn.

The result calculator 126_4 may calculate the calcification index of the target voxel TVX, based on the application result group CV. The result calculator 126_4 may add the intermediate results C0, C1, C2, . . . , and Cn. The result calculator 126_4 may analyze the summation result through the neural network. The result calculator 126_4 may analyze the summation result, based on a weight Wr and a bias br, and may calculate the calcification index of the target voxel TVX. For example, the result calculator 126_4 may generate an analysis result of the target voxel TVX by adjusting the summation result, adding the bias br, applying the result to a tanh function, and further multiplying the weight Wr. The weight Wr and the bias br may be included in the above-described parameter group.

The weight controller 126_5 may adjust the parameters Wc, bc, Wb, bb, Wr, and br included in the parameter group by comparing the analysis result (the calcification index of the target voxel TVX) with a preset result. The preset result may be a calcification index already known in the 3D image for learning. The weight controller 126_5 may adjust the parameter group such that the analysis result reaches a preset result. Based on the adjusted parameter group, the input voxel group IVX may be repeatedly analyzed. The adjusted parameter group may be updated in the learning model database 102 of FIG. 1.

Figure 6:
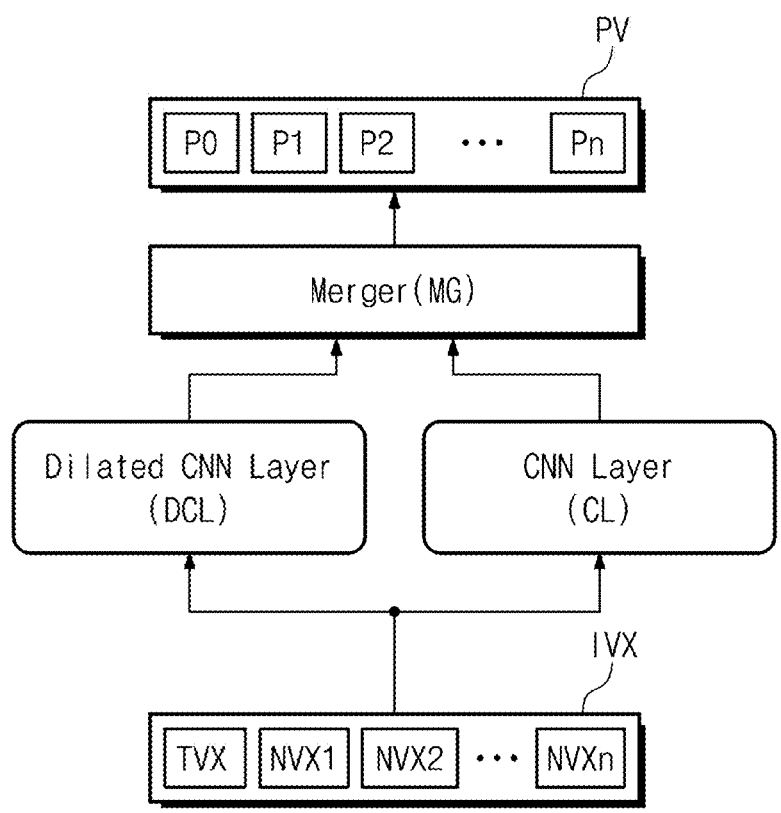
FIG. 6 is a diagram illustrating an exemplary hierarchical structure of an expression vector generator of FIG. 5.

FIG. 6 is a diagram illustrating an exemplary hierarchical structure of an expression vector generator of FIG. 5. FIG. 6 illustrates a neural network structure of the expression vector generator 126_1. This neural network structure may be at least a part of the above-described learning model. Referring to FIG. 6, the expression vector generator 126_1 may include a convolutional neural network (CNN) layer CL, a dilated CNN layer DCL, and a merger MG.

The CNN layer CL receives the input voxel group IVX including a target voxel TVX and the neighboring voxels NVX1 to NVXn. The CNN layer CL may calculate vectors (first vectors) of each of the target voxel TVX and the neighboring voxels NVX1 to NVXn. The CNN layer CL may calculate the first vectors by applying some of the parameters Wc and bc described in FIG. 5 to the input voxel group IVX. The CNN layer CL may calculate the first vectors through the convolutional neural network operation.

The dilated CNN layer DCL receives the input voxel group IVX including the target voxel TVX and the neighboring voxels NVX1 to NVXn in parallel with the CNN layer CL. The dilated CNN layer DCL may calculate vectors (second vectors) of each of the target voxel TVX and the neighboring voxels NVX1 to NVXn. The dilated CNN layer DCL may calculate the second vectors by applying some of the parameters Wc and bc described in FIG. 5 to the input voxel group IVX. The dilated CNN may be a CNN in which the filtering region is dilated by adding zero padding to the filter (weight). Accordingly, the second vectors may be results of analyzing global features of each voxel, and the first vectors may be results of analyzing local features of each of the voxels.

The merger MG may generate the expression vector PV by merging the first vectors and the second vectors. The expression vector PV may include a plurality of vectors P0 to Pn respectively corresponding to the target voxel TVX and the neighboring voxels NVX1 to NVXn. The vectors P0 to Pn with increased utility may be generated through merging of the first vectors and the second vectors.

Figure 7:
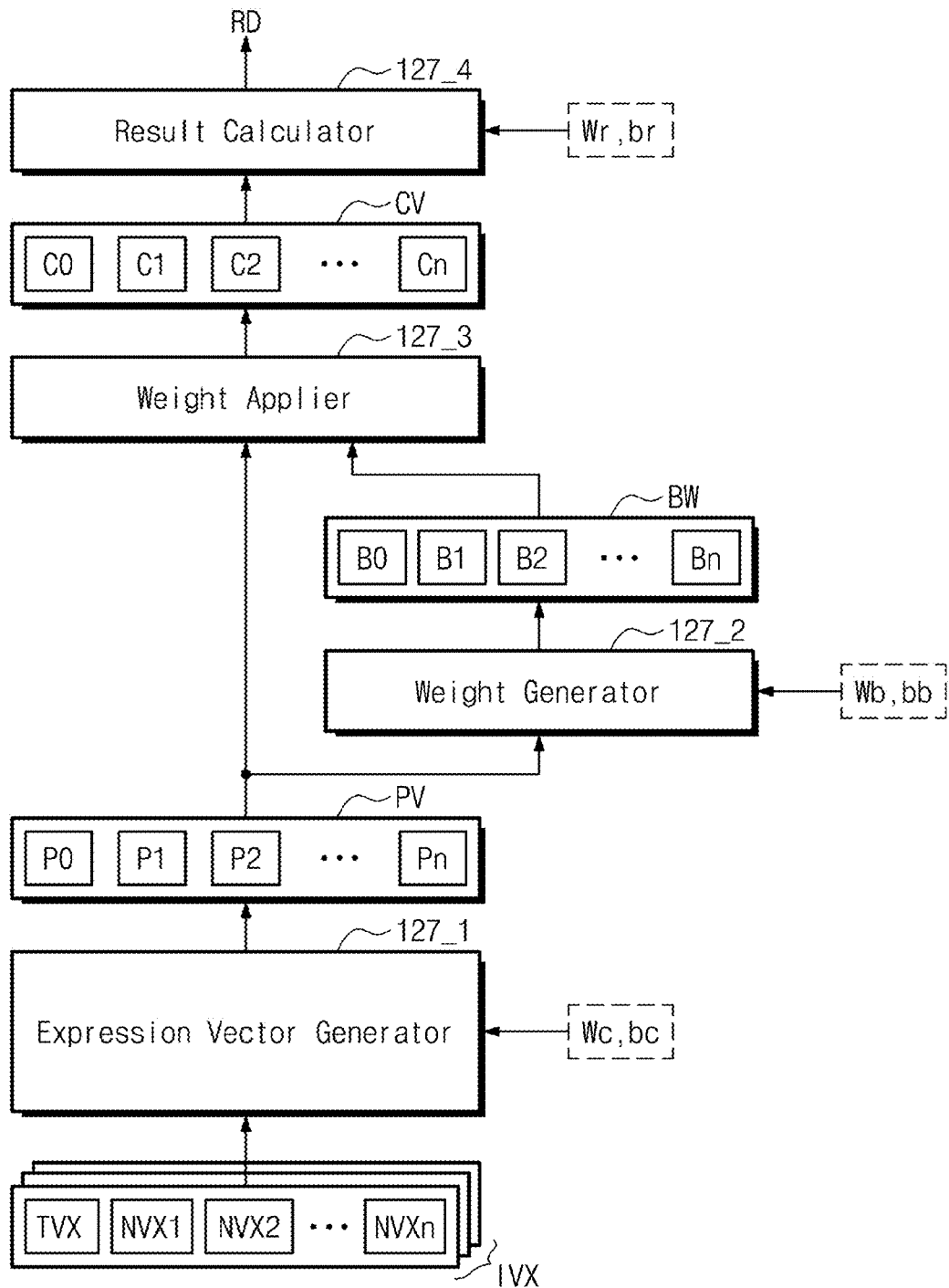
FIG. 7 is an exemplary block diagram of a predictor of FIG. 3.

FIG. 7 is an exemplary block diagram of a predictor of FIG. 3. The predictor 127 of FIG. 7 will be understood as an exemplary configuration that generates an analysis result such as the calcification index by applying the input voxel group IVX described in FIG. 4 to the learning model. Referring to FIG. 7, the predictor 127 may include an expression vector generator 127_1, a weight generator 127_2, a weight applier 127_3, and a result calculator 127_4. As described above, each of the components included in the predictor 127 may be implemented with hardware, firmware, software, or a combination thereof.

The expression vector generator 127_1 may generate the expression vector PV through the neural network operation on the input voxel group IVX. The expression vector PV may include a plurality of vectors P0, P1, P2, . . . , and Pn respectively corresponding to the target voxel TVX and the neighboring voxels NVX1, NVX2, . . . , and NVXn. The expression vector generator 127_1 may generate the vectors P0 to Pn corresponding to each of the target voxel TVX and the neighboring voxels NVX1 to NVXn, based on the weight Wc and the bias bc. The weight Wc and the bias bc may be a part of the parameter group adjusted in the learning step.

The weight generator 127_2 may generate the vector weight group BW, based on the expression vector PV. The vector weight group BW may include the vector weights B0, B1, B2, . . . , and Bn respectively corresponding to the vectors P0 to Pn. The weight generator 127_2 may generate the vector weights B0 to Bn so that the analysis result pays attention to a specific vector, using the neighbor attention mechanism. The weight generator 127_2 may generate the vector weight group BW, based on the weight Wb and the bias bb of the neighbor attention model. The weight Wb and the bias bb may be a part of the parameter group adjusted in the learning step.

As described above, the weight generator 127_2 may generate the correlation weights for generating the vector weight group BW. Further, the weight generator 127_2 may generate the vector weights B0 to Bn corresponding to the vectors P0 to Pn, respectively, by applying the correlation weights to the vectors P0 to Pn. This process may be substantially the same as the process of generating the vector weights B0 to Bn of the weight generator 126_2 described in FIG. 5.

The weight applier 127_3 may apply the vector weights B0 to Bn to the vectors P0 to Pn. The weight applier 127_3 may generate the application result group CV by multiplying a vector by a vector weight corresponding to each of the vectors P0 to Pn.

The result calculator 127_4 may generate an analysis result RD related to the calcification index of the target voxel TVX, based on the application result group CV. The result calculator 127_4 may analyze the application result group CV, based on the weight Wr and the bias br, and may calculate the calcification index of the target voxel TVX. The weight Wr and the bias br may be a part of the parameter group adjusted in the learning step. The result calculator 127_4 may calculate the final calcification index of the 3D image by merging the analysis results RD on each of the voxels and may determine the calcification of the coronary artery.

According to an embodiment of the inventive concept, an analysis result that indirectly reflects anatomical information such as blood vessels in a 3D image may be obtained by utilizing adjacent voxels of each of the voxels for analysis of a target voxel.

In addition, according to an embodiment of the inventive concept, an accuracy of determining calcification and an accuracy of a calcification index may be improved by applying a target voxel and neighboring voxels to a self-attention model.

The contents described above are specific embodiments for implementing the inventive concept. The inventive concept may include not only the embodiments described above but also embodiments in which a design is simply or easily capable of being changed. In addition, the inventive concept may also include technologies easily changed to be implemented using embodiments.

What is claimed is:

1. An image processing device comprising:
a voxel extractor configured to extract a target voxel and neighboring voxels adjacent to the target voxel from a 3D image; and
a learner configured to generate vectors corresponding to the target voxel and the neighboring voxels, respectively, to generate vector weights respectively corresponding to the vectors based on the vectors and a parameter group, to generate an analysis result of the target voxel by applying the vector weights to the vectors, and to adjust the parameter group based on the analysis result of the target voxel,
wherein the learner generates correlation weights for a target vector among the vectors by applying the parameter group to the vectors, and generates a vector weight corresponding to the target vector by adding values obtained by multiplying each of the vectors to each of the correlation weights, the target vector corresponding to the target voxel.

2. The image processing device of claim 1, wherein the number of the neighboring voxels is $(2n+1)^3-1$ with respect to a natural number 'n'.

3. The image processing device of claim 1, wherein the learner generates the correlation weights between the target vector and the vectors.

4. The image processing device of claim 1, wherein the learner generates the vectors through a convolutional neural network operation on each of the target voxel and the neighboring voxels.

5. The image processing device of claim 1, wherein the learner generates the vectors by merging a result of a convolutional neural network operation on each of the target voxel and the neighboring voxels and a result of a dilated convolutional neural network operation on each of the target voxel and the neighboring voxels, the convolutional neural network operation and the dilated convolutional neural network operation being performed in parallel.

6. The image processing device of claim 1, wherein the learner adjusts the parameter group until the analysis result is within a reference error from a preset result.

7. The image processing device of claim 1, wherein the 3D image is a computed tomography image, and wherein the analysis result is a calcification index.

8. An image processing device comprising:
a voxel extractor configured to extract a target voxel and neighboring voxels adjacent to the target voxel from a 3D image; and
a predictor configured to generate vectors corresponding to the target voxel and the neighboring voxels, respectively, to generate correlation weights for each of the vectors by applying a parameter group to the vectors, to generate a vector weight corresponding to each of the vectors by applying the correlation weights to the vectors, and to generate an analysis result of the target voxel by applying vector weights of the vectors to the vectors,
wherein the predictor generates target correlation weights for a target vector based on the target vector corresponding to the target voxel among the vectors, the vectors, and the parameter group, and
wherein the predictor generates a vector weight corresponding to the target vector by adding values obtained by multiplying each of the vectors to each of the target correlation weights.

9. The image processing device of claim 8, wherein the number of the neighboring voxels is $(2n+1)^3-1$ with respect to a natural number 'n'.

10. The image processing device of claim 8, wherein the parameter group includes parameter values depending on a correlation of the vectors for each of the vectors.

11. The image processing device of claim 8, wherein the voxel extractor sets each of a plurality of voxels included in the 3D image as the target voxel, and extracts the neighboring voxels, based on the set target voxel.

12. The image processing device of claim 11, wherein the predictor calculates a calcification index of the 3D image based on analysis results of the plurality of voxels.

13. A calcification analysis system comprising:
a computed tomography device configured to generate a 3D computed tomography image; and
an image processing device configured to extract a target voxel and neighboring voxels adjacent to the target voxel from the 3D computed tomography image, to generate vectors corresponding to the target voxel and the neighboring voxels, respectively, to generate vector weights respectively corresponding to the vectors based on a correlation among the vectors, and to calculate a calcification index of the target voxel by applying the vector weights to the vectors,
wherein the image processing device includes a learner configured to generate correlation weights for a target vector among the vectors by applying a parameter group to the vectors, to generate a vector weight corresponding to the target vector by adding values obtained by multiplying each of the correlation weights to each of the vectors, and to adjust the parameter group based on the calcification index, the target vector corresponding to the target voxel.

14. The calcification analysis system of claim 13, wherein the learner adjusts the parameter group until the calcification index is within a reference error from a preset result, and
wherein the adjusted parameter group is stored in a learning model database.

15. The calcification analysis system of claim 13, wherein the image processing device includes a predictor configured to generate correlation weights for each of the vectors by applying a parameter group provided from a learning model database to the vectors, to generate a vector weight corresponding to each of the vectors by applying the correlation weights for each of the vectors to the vectors, and to generate an analysis result of the target voxel by applying the vector weights of the vectors to the vectors.

16. The calcification analysis system of claim 15, wherein the image processing device further includes a voxel extractor configured to set each of a plurality of voxels included in the 3D image as the target voxel, and to extract the neighboring voxels based on the set target voxel, and
wherein the predictor calculates a calcification index of the 3D image based on analysis results of the plurality of voxels.

* * * * *